(12) United States Patent
Carlsson et al.

(10) Patent No.: US 10,137,198 B2
(45) Date of Patent: Nov. 27, 2018

(54) LIPID LAYER FORMING COMPOSITION FOR ADMINISTRATION ONTO A SURFACE OF A LIVING ORGANISM

(71) Applicant: LIPIDOR AB, Stockholm (SE)

(72) Inventors: Anders Carlsson, Stockholm (SE); Jan Holmback, Vaxholm (SE)

(73) Assignee: LIPIDOR AB, Stockholm (SE)

( * ) Notice: Subject to any disclaimer, the term of this patent is extended or adjusted under 35 U.S.C. 154(b) by 0 days.

(21) Appl. No.: 15/171,088

(22) Filed: Jun. 2, 2016

(65) Prior Publication Data

US 2016/0271256 A1    Sep. 22, 2016

Related U.S. Application Data

(62) Division of application No. 13/505,473, filed as application No. PCT/SE2010/000268 on Nov. 3, 2010, now Pat. No. 9,884,119.

(30) Foreign Application Priority Data

Nov. 3, 2009 (SE) ........................................ 0901409

(51) Int. Cl.

| | | |
|---|---|---|
| A61K 47/24 | (2006.01) | |
| A01N 25/02 | (2006.01) | |
| A61K 8/34 | (2006.01) | |
| A61K 8/37 | (2006.01) | |
| A61K 8/55 | (2006.01) | |
| A61K 8/63 | (2006.01) | |
| A61K 8/891 | (2006.01) | |
| A61K 9/08 | (2006.01) | |
| A61K 47/14 | (2017.01) | |
| A61Q 7/00 | (2006.01) | |
| A61Q 19/00 | (2006.01) | |
| A01N 37/18 | (2006.01) | |
| A61K 8/49 | (2006.01) | |
| A61K 8/89 | (2006.01) | |
| A61K 9/00 | (2006.01) | |
| A61K 31/167 | (2006.01) | |
| A61K 31/245 | (2006.01) | |
| A61K 31/4174 | (2006.01) | |
| A61K 31/573 | (2006.01) | |
| A61K 38/13 | (2006.01) | |
| A61K 47/10 | (2017.01) | |
| A61K 47/34 | (2017.01) | |
| A61Q 17/02 | (2006.01) | |

(52) U.S. Cl.
CPC .............. *A61K 47/24* (2013.01); *A01N 25/02* (2013.01); *A01N 37/18* (2013.01); *A61K 8/34* (2013.01); *A61K 8/342* (2013.01); *A61K 8/37* (2013.01); *A61K 8/4953* (2013.01); *A61K 8/553* (2013.01); *A61K 8/63* (2013.01); *A61K 8/89* (2013.01); *A61K 8/891* (2013.01); *A61K 9/0014* (2013.01); *A61K 9/08* (2013.01); *A61K 31/167* (2013.01); *A61K 31/245* (2013.01); *A61K 31/4174* (2013.01); *A61K 31/573* (2013.01); *A61K 38/13* (2013.01); *A61K 47/10* (2013.01); *A61K 47/14* (2013.01); *A61K 47/34* (2013.01); *A61Q 7/00* (2013.01); *A61Q 19/00* (2013.01); *A61Q 17/02* (2013.01)

(58) Field of Classification Search
None
See application file for complete search history.

(56) References Cited

U.S. PATENT DOCUMENTS

| | | | | |
|---|---|---|---|---|
| 4,952,560 A | * | 8/1990 | Kigasawa | ............ A61K 9/0014 514/21.92 |
| 5,336,692 A | * | 8/1994 | Gans | ...................... A61K 8/046 424/59 |
| 5,540,934 A | | 7/1996 | Touitou | |
| 5,795,575 A | | 8/1998 | Bombardelli et al. | |
| 6,086,860 A | | 7/2000 | Brewester | |
| 2003/0170194 A1 | * | 9/2003 | Piotrowiak | ............ A61K 8/046 424/70.12 |
| 2004/0234474 A1 | | 11/2004 | Berlat | |
| 2006/0147383 A1 | | 7/2006 | Mallard | |
| 2007/0041935 A1 | | 2/2007 | Salamone et al. | |
| 2008/0124296 A1 | * | 5/2008 | Elmasry | ................... A61K 8/11 424/70.19 |
| 2010/0048514 A1 | | 2/2010 | Topley et al. | |
| 2010/0080768 A1 | | 4/2010 | McGraw et al. | |
| 2012/0233728 A1 | | 9/2012 | Carlsson et al. | |

FOREIGN PATENT DOCUMENTS

| | | |
|---|---|---|
| EP | 0752247 A1 | 7/1997 |
| JP | 63-96114 A | 4/1988 |

(Continued)

OTHER PUBLICATIONS

English Translation of Office Action from Russian Patent App. No. 2012117954/15 (dated Mar. 6, 2015).

(Continued)

*Primary Examiner* — Mina Haghighatian
*Assistant Examiner* — Luke E Karpinski
(74) *Attorney, Agent, or Firm* — Cermak Nakajima & McGowan LLP; Malcolm K. McGowan

(57) ABSTRACT

A lipid layer forming composition comprises a volatile silicone oil of a boiling point above 180° C., a polar lipid, optionally a $C_2$-$C_4$ aliphatic alcohol, optionally a pharmacologically or cosmetically active agent or a protective agent. The lipid layer forming composition can be applied to a biological surface by spraying, dipping or brushing to form a stable polar lipid layer on the surface.

15 Claims, 3 Drawing Sheets

(56) References Cited

FOREIGN PATENT DOCUMENTS

| JP | 63-275518 | A | 11/1988 |
| JP | 2003-104826 | A | 9/2003 |
| JP | 2003-261435 | A | 9/2003 |
| JP | 2003-533491 | A | 11/2003 |
| JP | 2009-149624 | A | 7/2009 |
| WO | WO99/44585 | A1 | 9/1999 |
| WO | WO01/87344 | A1 | 11/2001 |
| WO | WO2006/056800 | A1 | 6/2006 |
| WO | WO2014/178789 | A1 | 11/2014 |

OTHER PUBLICATIONS

Patel, T., et al., "Menthol: A refreshing look at this ancient compound," J. Am. Acad. Dermatol. 2007;5:873-878.
Office Action for Swedish Patent App. No. 1550622-3 (dated Oct. 30, 2015).
Sene, C., et al., "Silicone as Excipients for Topical Pharmaceutical Application. The Silky Touch Product Family from Dow Corning," Product Information, Dow Corning, Jan. 1, 2001, pp. 1-12.
International Search Report, issued in PCT/SE2010/000268, dated Feb. 4, 2011.
Japanese Office Action, dated Jun. 13, 2014, Patent Application No. 2012-536745, with English translation thereof.
Japanese Office Action, dated May 15, 2015, Patent Application No. 2012-536745, with English translation thereof.
Japanese Office Action, dated Dec. 16, 2015, Patent Application No. 2012-536745, with English translation thereof.
Decision of Patent, dated Jan. 22, 2016, Patent Application No. 2012-536745, with English translation thereof.
Amendment and Argument, dated Nov. 25, 2014, Patent Application No. 2012-536745, with English translation thereof.
Amendment, dated Sep. 15, 2015, Patent Application No. 2012-536745, with English translation.
Notice of Appeal, dated Sep. 15, 2015, Patent Application No. 2012-536745, with English translation.
Amendment and Argument, dated Dec. 18, 2015, Patent Application No. 2012-536745, with English translation.
Office Action from Japanese Patent App. No. 2015-182024 (dated Aug. 30, 2016) with English language translation thereof.
Communication Pursuant to Article 94(3) EPC from European Patent App. No. 10828610.5 (Aug. 30, 2017).

* cited by examiner

LIPID LAYER FORMING COMPOSITION FOR ADMINISTRATION ONTO A SURFACE OF A LIVING ORGANISM

CONTINUING APPLICATION DATA

This application is a divisional of copending U.S. application Ser. No. 13/505,473, filed May 2, 2012, which is a U.S. National Stage Application under 35 USC 371 of PCT/SE2010/000268, filed Nov. 3, 2010, which claims priority from Swedish application 0901409-3, filed Nov. 3, 2009. The contents of these prior applications are incorporated herein in their entirety by reference

FIELD OF THE INVENTION

The present invention relates to a lipid layer forming composition optionally comprising a pharmacologically or cosmetically active agent or a protective agent for administration onto a surface of a living organism, in particular onto a membrane, such as the skin or a mucous membrane. The present invention also relates to a method of forming a lipid layer on a surface. The present invention furthermore relates to a layer capable of carrying a biologically active agent disposed on a surface of a living organism or a tissue or organ thereof and to a surface covered with such a lipid layer.

BACKGROUND OF THE INVENTION

In the pharmaceutical and cosmetic fields there is a need of a lipid composition capable of incorporating lipids and pharmacologically or cosmetically active compounds and of being evenly applicable to biological surfaces, in particular in form of a thin coherent layer. The lipid composition should be of low viscosity to facilitate delivery, in particular by spraying. While the viscosity of such a composition can be substantially reduced by adding a volatile solvent, the initially formed unstable coherent layer comprising lipid, pharmacologically or cosmetically active agent and solvent should change to a stable coherent layer by evaporation of the solvent within a time period as short as possible.

While a high solvent content is beneficial by reducing viscosity it requires more time for evaporation. In other words, a high solvent content in a lipid composition of the aforementioned kind extends the time period during which the applied composition is comparatively unstable. By "comparatively unstable" is understood the stability of an applied composition comprising substantial amounts of solvent in respect of the stability of the same composition after evaporation of all or substantially all solvent. Examples of such compositions include compositions for topical administration of pharmaceutically active compounds and compositions for skin care. Compositions rich in lipids are prone to form liquid crystals, a formation which is accompanied by high viscosity caused by high degree of local order.

WO 01/87344 A1 discloses a pharmaceutical or cosmetic composition comprising one or more pharmaceutically or cosmetically active agent, one or more organosilicon compound based on oligomeric or polymeric diorganosiloxane, and one or more phospholipid. When applied to the skin, the composition of WO 01/87344 A1 penetrates directly within a short period of time into the skin or into the external layers of plants treated with it, so that it cannot be rubbed off since it is rapidly absorbed into the interior of the body. For embodiments intended to be used topically in humans or animals the organosilicon compound of the composition has a boiling point varying between 15° C. and 150° C. at ambient pressure.

OBJECTS OF THE INVENTION

It is an object of the invention to provide a lipid composition for administration onto a surface of a living organism which is easily applicable and capable of forming a coherent stable oily lipid layer on the surface.

It is another object of the invention to provide such a lipid composition capable of carrying a biologically active agent.

Still another object of the invention is to provide such a lipid composition that does not cause swelling when applied to the skin.

A further object of the invention is to provide such a lipid composition that does not cause irritation nor give a burning feeling when applied on the skin.

Further objects of the invention will be evident from the following summary of the invention, preferred embodiments thereof described in form of examples, a drawing illustrating some of the preferred embodiments, as well as from the appended claims.

SUMMARY OF THE INVENTION

The present invention is based on the insight that silicone oils of a boiling point of 180° C. or higher, in particular of a boiling point of 200° C. or higher, can be used as an evaporating component of lipid carrier compositions for topical application, the compositions additionally comprising polar lipid and lower alcohol. "Evaporating component" indicates the capacity of silicone oils to evaporate, in spite of their high boiling point, within a short time upon application of the composition to the skin or other surface at ambient temperature or at a higher temperature. By their evaporation and the evaporation of the lower alcohol a layer of polar lipid is formed on the skin or other surface.

According to the present invention is disclosed a lipid carrier composition of the aforementioned kind, comprising or substantially consisting of polar lipid, volatile silicone oil of the invention, and a lower alcohol. The lipid carrier composition of the invention is useful for providing a stable coherent polar lipid layer on a surface of a living organism.

By incorporation of a pharmacologically or cosmetically active agent or a protective agent the lipid carrier composition of the invention is transformed to a pharmaceutical or cosmetic lipid composition of the invention or a protective lipid composition of the invention. The pharmaceutical, cosmetic or protective lipid composition of the invention comprising an active agent of the aforementioned kind can be used for delivering the agent on a surface of a living organism on which it is applied. A preferred surface is the skin or a mucous membrane such as the nasal or gastric mucous membrane. Another preferred surface is a plant surface, such as the surface of a grain or seed.

The present invention is based on the finding that a particular class of solvents, volatile silicone oils, optionally in combination with a lower aliphatic alcohol, are particularly useful in formulating a lipid carrier composition comprising a polar lipid. After application onto a biological surface the lipid carrier composition of the invention forms an unstable polar lipid layer from which the volatile silicone oil and, if present, the lower aliphatic alcohol, evaporates readily, leaving a stable lipid layer substantially consisting of polar lipid. Correspondingly, a stable polar lipid layer comprising a pharmaceutically or cosmetically active agent is formed by incorporating the active agent into the lipid carrier composition of the invention, applying it to a biological surface, and allowing the solvent or combination of solvents to evaporate. The low viscosity of the carrier composition of the invention and the pharmaceutical or cosmetic composition of the invention seems to be due to the inability of polar lipids to form lyotropic liquid crystals, such as lamellar, hexagonal and various cubic phases of high viscosity. The lipid carrier composition and the pharmaceutical or cosmetic composition of the invention are clear and of low viscosity even at concentrations of polar lipid as high as 20% by weight.

In contrast, polar lipid compositions corresponding to those of the invention but in which the silicone oil component is substituted by a corresponding amount of water are slightly viscous dispersions at low polar lipid concentrations or thick gels at higher polar lipid concentration tested, for instance 20% by weight of the composition. The high viscosity of the latter composition does not allow administration by spraying. By using the volatile silicone oil as the diluent instead of water, it is possible to incorporate a surprisingly high amount of polar lipid while only insignificantly affecting viscosity.

Silicone oils of personal care grade or pharmaceutical grade useful in the invention are known in the art. Examples of useful silicone oils include dekamethyl-cyclopentasiloxane (Dow Corning® 245 Fluid) and dodekamethylcyclohexasiloxane (Dow Corning® 246 Fluid). While pentasiloxanes and hexasiloxanes are preferred, hepta- and octasiloxanes are also potentially useful. The silicone oils may be cyclic siloxanes, that is, cyclomethicones, or linear siloxanes, that is, dimethicones. The silicone oils of the invention can be used in pure form or in admixture. While permethyl substitution is preferred, one or more methyl groups of a siloxane can be substituted by lower alkyl, in particular by ethyl, propyl or isopropyl. Siloxanes partially or fully substituted by lower trifluoroalkyl, in particular trifluoromethyl and pentafluoroethyl, are also useful in the invention.

In addition to chemical inertness the usefulness of the silicone oil of the invention is determined by its volatility. In spite of its high boiling point above 180° C., in particular above 200° C., the silicone oil of the invention evaporates readily due to the low heat of vaporization of this class of compounds. In the invention a silicone oil having a heat of vaporization (kJ/kg) at 25° C. of from about 100 kJ/kg to about 300 kJ/kg, more preferred of from about 120 kJ/kg to about 200 kJ/kg is particularly useful. Even more preferred is a silicone oil having a heat of vaporization of from 140 kJ/kg to about 180 kJ/kg at 25° C.

The silicone oil of the invention provides the carrier composition and the pharmaceutical or cosmetic composition of the invention with at least the following advantageous features: i) the ability to incorporate high contents of polar lipid material; ii) the formation of thermodynamically stable solutions; iii) the low viscosity of the solutions formed making them suitable for, e.g., spraying, dropping, painting or instilling.

The lower aliphatic alcohol of the invention is a $C_2$ to $C_4$ alcohol or a mixture of such alcohols. Preferred examples of alcohols are ethanol and 2-propanol. Other useful alcohols are glycerol and 1,2-propanediol. Solvents other than lower alcohols may also be used, such as dimethyl sulfoxide and N-methyl-2-pyrrolidone. In applications with less stringent biocompatibility requirements solvents such chloroform, dichloromethane, pyridine, hexane, and methanol can be used.

The polar lipid of the invention is preferably a membrane lipid such as a phospholipid, a glycolipid, a sphingolipid or a mixture thereof. A particularly preferred phospholipid is phosphatidyl choline. Other preferred phospholipids are phosphatidyl ethanolamine and phosphatidyl inositol. A particularly preferred glycolipid is galactolipid. A preferred galactolipid is digalactosyl-1,2-diacylglycerol as such or in admixture with other galactolipids and/or phospholipids and/or sphingolipids.

Technical scale commercial polar lipids useful in the invention contain substantial amounts of non-polar lipids, so as to be composed of up to about 50 to 60% by weight of non-polar lipid. Thus, according to a further preferred aspect of the invention, the polar lipid component of the carrier composition or the pharmaceutical or cosmetic composition of the invention comprises a non-polar lipid in an amount of up to 30% by weight or more, such as up to 50% or 60% by weight and even up to 75% by weight. Non-polar lipids as components of polar lipids are preferably mono- and diglycerides and their mixtures, in particular monoglycerides. In a polar lipid of the invention a higher proportion of mono- and diglyceride, in particular of monoglyceride, can be tolerated than one of triglyceride.

The use of a lower aliphatic alcohol such as absolute ethanol for the dissolution of the oily polar lipid of the invention is particularly useful with a lipid of a low chain-melting temperature. The chain-melting temperature is the temperature at which the acyl chains of a membrane lipid undergo a phase transition in an excess of water, from a solid-like state to a melted or liquid-like state. Membrane lipid materials like Lipoid S75, Lipoid S45, Phospholipon 50, Lipoid S 100, and DOPC all have chain-melting temperatures below 0° C. and can thus be readily dissolved in $C_2$ to $C_4$ alcohol, in particular ethanol, at concentrations up to 50% by weight and even higher.

To produce the carrier composition of the invention the polar lipid, in particular a membrane lipid mixture such as a lecithin or fractionated oat oil, is dissolved in $C_2$ to $C_4$ alcohol and then diluted with a volatile silicone oil, resulting in a low-viscous, sprayable, homogenous liquid. A typical example of such a composition is one consisting of 49% DC 345, 37% fractionated oat oil (LTP Lipid Technologies Provider AB, Sweden), and 14% by weight of absolute ethanol. Fractionated oat oil is obtained from crude oat oil and is enriched in polar lipids. It typically contains about 50% by weight of non-polar lipid, such as triacylglycerol and diacylglycerol, and about 50% by weight of polar lipid, such as phospholipid and galactolipid. Typically, the content of digalactosyldiacylglycerol in a fractionated oat oils is about 20% by weight. Suitable fractionated oat oils are disclosed, for instance, in WO 99/44585 A1.

Lipids like phosphatidyl ethanolamine, for instance dioleylphosphatidyl ethanolamine (DOPE), or sphingolipid, for instance sphingomyelin, can also be used as a polar lipid of the invention as such or in admixture with other polar lipids. DOPE has a chain-melting temperature of −16° C. in water and can be dissolved in absolute ethanol at 50% by weight or higher at elevated temperatures (>60° C.). Such solution can be diluted with volatile silicone oil such as DC 345, resulting in a clear, low-viscous liquid.

Although small amounts of water, such as 1% or 2% and even up to about 5% by weight can be tolerated, the lipid carrier composition of the invention is preferably substantially water-free, in particular has a water content of less than 5% by weight, preferably of less than 2% or 1% by weight and even less than 0.5% by weight or 0.2% by weight.

The pharmacologically or cosmetically active agent or the protective agent can be incorporated in the lipid carrier composition in an amount of from 0% to 2% by weight or to 5% by weight and even up to 25% by weight or more in respect of total non-volatile components of the carrier composition, in particular polar lipid, remaining upon evaporation of its volatile components.

The pharmacologically active agent for incorporation into the lipid carrier composition of the invention is preferably selected from the group consisting of: antimicrobial agent; antibiotic; antimycotic agent; antibacterial agent; antifungal agent; antiviral agent; antiseptic; anti-phlogistic; anti-pruritic agent; anti-psoriatic agent; antitussive agent; anti-alopecia agent; anti-acne agent; anti-inflammatory agent; anti-ulcer agent; local anaesthetic; immune response modifying agent.

In particular, the pharmacologically active agent of the invention is selected from: antibacterial agents, such as oxytetracycline, fusidic acid, gentamycine, mupirocin, retapamulin (and pharmaceutically acceptable salts and derivatives thereof); antimycotic agents, such as nystatin, clotrimazole, miconazole, econazole, ketoconazole, bifonazole, and combinations of imidazole and triazole derivatives, ciclopirox, terbinafine, fluconazole, and amorolfine (and pharmaceutically acceptable salts and derivatives thereof); antiviral agents, such as aciclovir, valaciclovir, penciclovir, famciclovir, foscarnet (sodium phosphoneformate hexahydrate) and docosanol (and pharmaceutically acceptable salts and derivatives thereof); antiseptics, such as chlorhexidine and hydrogen peroxide; anti-inflammatory agents (glucocorticoids), such as hydrocortisone, clobetasone, triamcinolone, betamethasone, mometasone, and clobetasol (and pharmaceutically acceptable salts and derivatives thereof); antiphlogistics/analgesics (NSAID's), such as acetylsalicylic acid, diclofenac, and ibuprofen (and pharmaceutically acceptable salts and derivatives thereof); antipruritic agents, such as glucocorticoids, for example, hydrocortisone, clobetasone, and betamethasone, and local anaesthetics, for example, lidocaine and prilocaine (and pharmaceutically acceptable salts and derivatives thereof); antpsoriatic agents, such as calcipotriol and cyclosporine A (and pharmaceutically acceptable salts and derivatives thereof); agents for treatment of eczema and atopic dermatitis: tacrolimus and pimecrolimus (and pharmaceutically acceptable salts and derivatives thereof); antiglaucomateous agents, such as timolol, betaxolol, latanoprost, bimatoprost, and travoprost (and pharmaceutically acceptable salts and derivatives thereof); local anaesthetics, such as lidocaine, prilocaine, ropivacaine, mepivacaine, bupivacaine, levobupivacaine, benzocaine, and tetracaine (and pharmaceutically acceptable salts and derivatives thereof); agents for erectile dysfunction, such as alprostadil (prostaglandin E1) (and pharmaceutically acceptable salts and derivatives thereof); anti-dandruff agents, such as selenium sulphides, piroctone oleamine and ketoconazole; anti-alopecia agents, such as minoxidil (and pharmaceutically acceptable salts and derivatives thereof); anti-acne agents, such as tretinoin (retinoic acid), adapalene, benzoyl peroxide, clindamycin, azelaic acid (and pharmaceutically acceptable salts and derivatives thereof); wound healing agents, such as fusidic acid (and pharmaceutically acceptable salts and derivatives thereof).

The cosmetically active agent for incorporation into the lipid carrier composition of the invention is preferably selected from the group consisting of: antiperspirant; antisudoral agent; antidandruff agent; glidant; moisturizing agent.

The protective agent for incorporation into the lipid carrier composition of the invention is preferably selected from the group consisting of: insect repellent; UV absorbing agent; antifungal agent; antibacterial agent; antiviral agent.

Examples of other agents for incorporation into the lipid carrier composition of the invention are: insect repellents, such as N,N-diethyl-m-toluamide (DEET), icaridine, and ethyl butyl acetylaminopropionate (and salts and derivatives thereof); UV sunscreens, both physical and chemical, such as titanium dioxide, benzophenon-3, butyl methoxydibenzoylmethane, ethyl hexyl methoxycinnamate, and 4-aminobenzoic acid (PABA) (and salts and derivatives thereof); tanning agents, such as dihydroxyacetone.

The cosmetically active agent for incorporation into the lipid carrier composition of the invention is preferably selected from the group consisting of: antiperspirant; antisudoral agent; antidandruff agent; glidant; moisturizing agent. Preferred antidandruff agents include piroctone oleamine and ketoconazole.

In addition to the pharmacologically active agent, the cosmetically active agent or the protective agent the respective composition of the invention can contain a counterirritant, in particular one selected from methyl salicylate, capsaicin, camphor and menthol.

According to the present invention is also disclosed a pharmaceutical composition for administration onto a surface of a living organism comprising a pharmacologically active agent in the lipid carrier composition of the invention.

According to the present invention is furthermore disclosed a cosmetic composition comprising a cosmetically active agent in the lipid carrier composition of the invention.

The pharmacologically or cosmetically active agent can be dissolved or dispersed in the carrier composition or in the silicone oil, the lower alcohol, if present, and/or the oily polar lipid used for formulating the pharmaceutical or cosmetic composition of the invention.

According to a preferred aspect of the invention the carrier composition of the invention comprises or consists of from 10% by weight to 30% by weight of phospholipid, from 10% by weight to 30% by weight of $C_2$ to $C_4$ alcohol, in particular ethanol, the remainder being a volatile silicone oil, with the proviso that the content of volatile silicone oil is 50% by weight or more.

According to a further preferred aspect of the invention, the pharmaceutical, cosmetic or protective composition of the invention comprises or consists of from 10% by weight to 30% by weight of phospholipid, from 10% by weight to 30% by weight of $C_2$ to $C_4$ alcohol, in particular ethanol, from 0.01% by weight to 30% by weight, in particular from 0.01% by weight to 1% by weight or to 2% by weight or to 5% by weight, of pharmaceutically or cosmetically active agent or of protective agent, the remainder being a volatile silicone oil, with the proviso that the content of volatile silicone oil is 40% by weight or more.

According to another preferred aspect of the invention is disclosed a pharmaceutical carrier composition, that is, a composition of the invention which does not comprise pharmaceutically or cosmetically agent or protective agent but into which such agent can be incorporated. The carrier composition can comprise or consist of from about 30% by weight to about 90% by weight of silicone oil, from about 5% by weight to about 45% by weight of polar lipid, and from about 5% by weight to about 45% by weight of $C_2$ to $C_4$ alcohol, in particular ethanol, optionally 5% by weight or less of water, in particular less than 1% by weight of water.

According to still another preferred aspect of the invention is disclosed a pharmaceutical, cosmetic or protective carrier composition substantially consisting of polar lipid, volatile silicone oil and ethanol in percent by weight proportions comprised by area F in the phase diagram of FIG. 3, optionally comprising 5% by weight or less, in particular 1% by weight or less, of water.

By addition of a desired amount of pharmaceutical, cosmetic or protective agent of the invention, in particular of from 0.01% by weight to 2% by weight or to 5% by weight and even up to 15% by weight or up to 25 by weight in respect of polar lipid, the carrier composition of the invention can be transformed into the pharmaceutical, cosmetic or protective composition of the invention.

The pharmaceutical, cosmetic or protective composition of the invention can be applied to a dry or a humid biological surface by any suitable method, such as by spraying, dipping, brushing, dropping, rubbing in.

The invention will now be described in greater detail by reference to a number of Examples illustrated in a drawing.

SHORT DESCRIPTION OF THE FIGURES

DESCRIPTION OF PREFERRED EMBODIMENTS

Materials

TABLE 1

Figure 1:
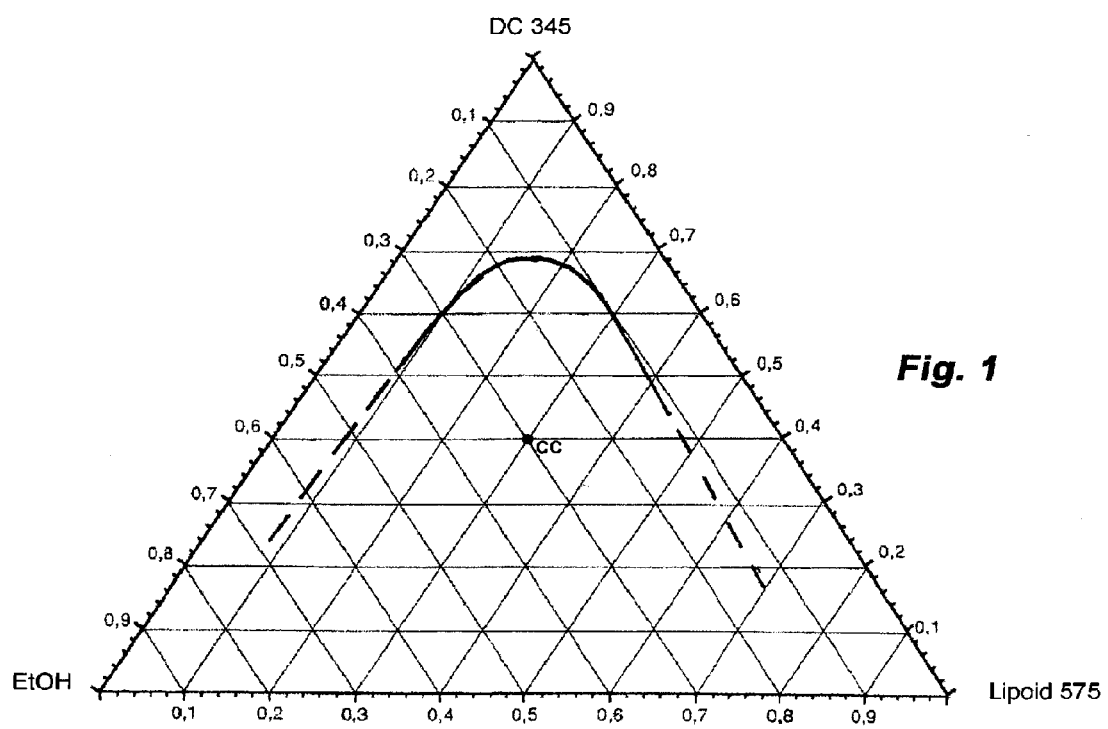
FIG. 1 is a ternary phase diagram of a carrier composition of the invention.

Silicone oils and lipids used in the formulation experiments

| Short name | Supplier, trade name | Chemical name, CAS No. | Lot No. |
|---|---|---|---|
| DC 345 | Dow Corning ® 345 Fluid | Dekamethyl-cyclopentasiloxane, 541-02-6 | 5627357 |
| DC 245 | Dow Corning ® 245 Fluid | Dekamethyl-cyclopentasiloxane, 541-02-6 | 5480964 |
| DC 246 | Dow Corning ® 246 Fluid | Dodekamethyl-cyclohexasiloxane, 540-97-6 | 5264620 |
| DMPC | Lipid DMPC | Dimyristoyl phosphatidylcholine, 13699-48-4 | 562212-1/13 |
| DPPC | Lipid DPPC | Dipalmitoyl phosphatidylcholine, 2644-64-6 | 563086-1/94 |
| DOPC | Lipid DOPC | Dioleoyl phosphatidylcholine, 10015-85-7 | 566073-1/32 |
| DMPG | Lipid DMPG, Na salt | Dimyristoyl phosphatidylglycerol sodium salt, 200880-40-6 | 602081-1/10 |
| DPPG | Lipid DPPG, Na salt | Dipalmitoyl phosphatidylglycerol sodium salt, 200880-41-7 | 603032-1/36 |
| DMPE | Lipid DMPE | Dimyristoyl phosphatidyl-ethanolamine, 20255-95-2 | 699201-1/05 |
| DPPE | Lipid DPPE | Dipalmitoyl phosphatidyl-ethanolamine, 3026-45-7 | 653004-1/19 |
| DOPE | Lipid DOPE | Dioleoylphosphatidyl-ethanolamine, 2462-63-7 | 656006-01/012 |

TABLE 1-continued

Silicone oils and lipids used in the formulation experiments

| Short name | Supplier, trade name | Chemical name, CAS No. | Lot No. |
|---|---|---|---|
| MOG | Fluka (Sigma-Aldrich), Monoolein | Monooleoylglycerol, 25496-72-4 | 1384627 |
| MCM | Aarhus Karlshamn, Akoline MCM | Medium chain monoglycerides | 8192270 |
| CPL-GL | LTP, CPL ®-Galactolipid | Chromatographically purified galactolipids | KGL06002 |
| O65 | Swedish Oat Fiber, Oatwell 65 oat oil | Galactolipid enriched oat oil | PL 090219 |
| Chol | Sigma-Aldrich, Cholesterol | Cholesterol, 57-88-5 | 057K0683 |
| IPM | Croda, Crodamol IPM | Isopropyl myristate, 110-27-0 | LB03845 |
| S45 | Lipoid S45 | Soy bean lecithin, 8002-43-5 | 745303-1/926 |
| S75 | Lipoid S75 | Soy bean lecithin, 8002-43-5 | 776132-07/918 |
| S100 | Lipoid S100 | Soy bean lecithin, 8002-43-5 | 790551-7/910 |

TABLE 2

Active substances used in the formulation experiments*)

| Active substance | CAS No. | Supplier | Lot No. |
|---|---|---|---|
| Lidocaine | 137-58-6 | Sigma-Aldrich | 047K0080 |
| Hydrocortisone | 50-23-7 | Sigma-Aldrich | 010M1568 |
| Dihydroxyacetone | 96-26-4 | Sigma-Aldrich | 04306BJ-409 |
| LL-37 | — | PolyPeptide Laboratories A/S | 1013/11 |
| DPK-060 | — | Dermagen | 0508074339 |
| Oxytocin acetate | 50-56-6 | Sigma-Aldrich | 068K8762 |

*)Further information is given in the EXAMPLES

Alcohols used in the formulation experiments were ethanol 99.9% ("EtOH", VWR), 2-propanol HPLC grade ("IPA", Rathburn), glycerol 99.5% ("Gro", VWR) and 1,2-propanediol, Ph. Eur. ("PD", Fluka/Sigma-Aldrich). The materials used in the formulation experiments were provided by the following suppliers: Dow Corning Corp., Midland, Mich., USA; Lipoid GmbH, Ludwigshafen, Germany; Aarhus Karlshamn Sweden AB, Karlshamn, Sweden; LTP Lipid Technologies Provider AB, Karlshamn, Sweden; Swedish Oat Fiber AB, Väröbacka, Sweden; Sigma-Aldrich, St. Louis, Mo., USA; Croda, Goole, East Yorkshire, UK; Rathburn Chemicals Ltd, Walkerburn, Scotland, UK; VWR International AB, Spånga, Sweden; PolyPeptide Laboratories A/S, Hillerød, Denmark; Dermagen AB, Lund, Sweden.

EXAMPLE 1

Formulation of a Local Anaesthetic: Lidocaine and Lidocaine Hydrochloride

| Composition A: | |
|---|---|
| Ingredient | % (w/w) |
| Lidocaine (Sigma L7757) | 3.9 |
| Phospholipid (Lipoid S75) | 19.5 |

-continued

Composition A:

| Ingredient | % (w/w) |
|---|---|
| Absolute ethanol | 19.5 |
| Volatile silicone oil (DC 345) | 57.1 |

Composition B:

| Ingredient | % (w/w) |
|---|---|
| Lidocaine hydrochloride (Sigma L5647) | 2.0 |
| Phospholipid (Lipoid S75) | 20.0 |
| Absolute ethanol | 20.0 |
| Volatile silicone oil (DC 345) | 58.0 |

The phospholipid was dissolved in absolute ethanol at a concentration of 50.0% (w/w). Complete dissolution of the phospholipid was promoted by short ultrasonication in a bath-type sonicator at about 40° C.

To a pre-weighed amount of lidocaine and lidocaine hydrochloride, respectively, was added the ethanolic phospholipid solution. The mixtures were gently heated and sonicated until clear solutions had been formed. The solutions were diluted with volatile silicone oil to obtain light brown to yellow solutions, which were stored in air-tight glass vials at room temperature. The appearance of compositions (compositions A and B) was unchanged for more than a month at room temperature. No signs of phase separation or precipitation and subsequent sedimentation were observed. This indicates excellent physical stability.

EXAMPLE 2

Formulation of a Local Anaesthetic: Benzocaine

A pre-weighed amount of benzocaine was dissolved in a 50% (w/w) ethanolic phospholipid, prepared as described in Example 1. The solution was diluted with the volatile silicone oil. The resulting clear, light brown to yellow solution was stored in an air-tight glass vial at room temperature. The appearance of the composition (composition C) was unchanged for more than a month at room temperature. No signs of phase separation or precipitation and subsequent sedimentation were observed, which indicates excellent physical stability.

Composition C:

| Ingredient | % (w/w) |
|---|---|
| Benzocaine (Fluka 06952) | 4.0 |
| Phospholipid (Lipoid S75) | 20.2 |
| Absolute ethanol | 20.2 |
| Volatile silicone oil (DC 345) | 55.6 |

EXAMPLE 3

Formulation of an Insect Repellent: N,N-Diethyl-m-Toluamide (DEET)

Composition D:

| Ingredient | % (w/w) |
|---|---|
| DEET (Aldrich D10,095-1) | 13.4 |
| Phospholipid (Lipoid S75) | 16.7 |
| Absolute ethanol | 16.7 |
| Volatile silicone oil (DC 345) | 53.2 |

To a pre-weighed amount of DEET was added 50% (w/w) ethanolic phospholipid prepared as described in Example 1. The obtained clear solution was diluted with the volatile silicone oil. The resulting clear, light brown to yellow solution was stored in an air-tight glass vial at room temperature. The appearance of the composition (composition D) was unchanged for more than a month at room temperature. No signs of phase separation or precipitation and subsequent sedimentation were observed, which indicates excellent physical stability.

EXAMPLE 4

Formulation of an Antifungal Agent: Econazole Nitrate

| Ingredient | Composition E: % (w/w) | Composition F: % (w/w) | Composition G: % (w/w) |
|---|---|---|---|
| Econazole nitrate (Sigma E4632) | 2.3 | 1.1 | 1.5 |
| Phospholipid (Lipoid S75) | 29.1 | 14.5 | 21.2 |
| Absolute ethanol | 29.1 | 14.5 | 21.2 |
| Volatile silicone oil (DC 345) | 39.5 | 69.9 | 56.1 |

Three compositions (E, F, G) were prepared. To pre-weighed amounts of econazole nitrate was added 50% (w/w) ethanolic phospholipid prepared as described in Example 1. After treatment in a bath-type sonicator at about 37° C., the obtained clear golden brown solutions were diluted with the volatile silicone oil. The resulting clear, light golden brown solutions were stored in air-tight glass vials at room temperature. composition F was prepared by diluting a portion of composition E with volatile silicone oil.

The appearance of compositions E and F changed within a few days (slight sedimentation was observed in both samples) and therefore cannot be considered stable. On the other hand, the appearance of Composition G was unchanged for more than a month at room temperature. No signs of phase separation or precipitation and subsequent sedimentation were observed, indicating excellent physical stability.

EXAMPLE 5

Formulation of a Glucocorticoid: Betamethasone 17-Valerate

Three compositions (H, I, J) were prepared. To pre-weighed amounts of betamethasone 17-valerate was added 50% (w/w) ethanolic phospholipid prepared as described in Example 1. After treatment in a bath-type sonicator at about 37° C., clear golden brown solutions were obtained. The solutions were diluted with the volatile silicone oil and the resulting mixtures stored in air-tight glass vials at room temperature.

Composition I was prepared by diluting a portion of Composition H with volatile silicone oil. Composition I was unstable since it formed immediately a milky dispersion, which separated within a few days. Compositions H and J formed clear, light golden brown solutions. They showed no signs of phase separation or precipitation and subsequent sedimentation after storage for one month at room temperature. This indicates excellent physical stability.

| Ingredient | Composition H: % (w/w) | Composition I: % (w/w) | Composition J: % (w/w) |
|---|---|---|---|
| Betamethasone 17-valerate (Sigma B0515) | 0.5 | 0.1 | 0.1 |
| Phospholipid (Lipoid S75) | 13.3 | 2.7 | 21.1 |
| Absolute ethanol | 13.3 | 2.7 | 21.1 |
| Volatile silicone oil (DC 345) | 72.9 | 94.5 | 57.7 |

EXAMPLE 6

Formulation of an Anti-Psoriatic Agent: Cyclosporin A

| Composition K: | |
|---|---|
| Ingredient | % (w/w) |
| Cyclosporin A (Sigma, 30024) | 0.4 |
| Phospholipid (Lipoid S75) | 16.0 |
| Absolute ethanol | 16.0 |
| Volatile silicone oil (DC 345) | 67.6 |

To a pre-weighed amount of cyclosporin A was added a 50% (w/w) ethanolic phospholipid solution, prepared as described in Example 1. After treatment in a bath-type sonicator at about 35° C., a clear solution was obtained. The solution was diluted with the volatile silicone oil to form a clear, light brown to yellow solution, which was stored in an air-tight glass vial at room temperature. The appearance of the composition (composition K) was unchanged for more than a month at room temperature. No signs of phase separation or precipitation and subsequent sedimentation were observed. This indicates excellent physical stability.

EXAMPLE 7

Formulation of an Anti-Alopecia Agent: Minoxidil

Three compositions (M, N, O) were prepared. To pre-weighed amounts of minoxidil was added a 33% (w/w) ethanolic phospholipid solution, ethanol, and 50% (w/w) ethanolic phospholipid. After treatment in a bath-type sonicator at about 35° C., the resulting mixtures were diluted with the volatile silicone oil and stored in air-tight glass vials at room temperature.

| Ingredient | Composition M: % (w/w) | Composition N: % (w/w) | Composition O: % (w/w) |
|---|---|---|---|
| Minoxidil (Tripharma) | 0.67 | 0.98 | 0.65 |
| Phospholipid (Lipoid S75) | 21.98 | — | 17.75 |
| Absolute ethanol | 21.98 | 40.27 | 35.49 |
| Volatile silicone oil (DC 345) | 55.37 | 58.75 | 46.11 |

The appearance of composition O stayed unchanged for more than two months at room temperature, i.e., no signs of phase separation or precipitation and subsequent sedimentation were observed. This indicates excellent physical stability. Composition M did not show complete dissolution of minoxidil, whereas Composition N started to precipitate shortly after preparation. Thus compositions M and N did not meet the criteria of one-month stability when stored in a closed container at room temperature.

EXAMPLE 8

Miscibility Test

Presented in Table 3 are miscibility data of ethanolic phospholipid solutions with either volatile silicone oil or water. The mixtures with a low content of PL/ethanol in the silicone oil had a clear appearance immediately after preparation, but separated within a month at room temperature. The composition with a concentration of PL/ethanol of 20% was miscible with the volatile silicone oil, did not change in appearance during this time period and can thus be considered to be physically stable.

TABLE 3

Dilution of ethanolic phospholipid (PL; Lipoid S75) solutions with volatile silicone oil (DC 345) and water, respectively. All percentages are by weight

| Composition of EtOH solution | EtOH solution | Volatile silicone oil | Water | Conc. of PL | Conc. of ethanol | Conc. of diluent | Appearance directly after dilution | Appearance after one month at RT |
|---|---|---|---|---|---|---|---|---|
| 75.0% PL | 1.01 g | 1.60 g | — | 29.0% | 9.7% | 61.3% | Opaque dispersion, clear on warming | — |
| 75.0% PL | 1.01 g | 2.22 g | — | 23.5% | 7.8% | 68.7% | Opaque dispersion, clear on warming | — |
| 50.0% PL | 5.00 g | 7.50 g | — | 20.0% | 20.0% | 60.0% | Clear, low-viscous light brown solution | Unchanged |

TABLE 3-continued

Dilution of ethanolic phospholipid (PL; Lipoid S75) solutions with volatile silicone oil (DC 345) and water, respectively. All percentages are by weight

| Composition of EtOH solution | EtOH solution | Volatile silicone oil | Water | Conc. of PL | Conc. of ethanol | Conc. of diluent | Appearance directly after dilution | Appearance after one month at RT |
|---|---|---|---|---|---|---|---|---|
| 50.0% PL | 5.00 g | — | 7.52 g | 20.0% | 20.0% | 60.0% | Viscous gel | Unchanged |
| 50.0% PL | 0.50 g + 4.51 g neat EtOH | 7.51 g | — | 2.0% | 38.0% | 60.0% | Clear, low-viscous light yellow, opaque solution | |
| 50.0% PL | 0.50 g | 4.51 g | — | 5.0% | 5.0% | 90.0% | Clear, low-viscous light yellow solution | Phase separation |
| 50.0% PL | 0.50 g | — | 4.52 g | 5.0% | 5.0% | 90.0% | Homogeneous viscous dispersion | Unchanged |
| 33.3% PL | 0.50 g | 4.50 g | — | 3.3% | 6.7% | 90.0% | Clear, low-viscous light yellow solution | Phase separation |
| 33.3% PL | 0.50 g | — | 4.52 g | 3.3% | 6.7% | 90.0% | Homogeneous dispersion | Unchanged |

The phospholipid of Table 1 is Lipoid S75 manufactured by Lipoid GmbH, Ludwigshafen, Germany. This phospholipid material from soybean contains about 68-73% of phosphatidyl choline (PC). Other suitable phospholipid materials are, for example, Lipoid S45, Phospholipon 50, and Lipoid 5100, all made from soybean and manufactured by Lipoid GmbH, covering a range of PC content of about 50% up to 100%. Further suitable phospholipids are the synthetic dioleyl phosphatidylcholine (DOPC), dimyristyl phosphatidylcholine (DMPC), and dipalmitoyl phosphatidylcholine (DPPC).

EXAMPLE 9

Phase Diagram

FIG. 1 illustrates an exemplary phase diagram of the ternary system of the polar lipid carrier composition of the invention: polar lipid (Lipoid S75)/$C_2$-$C_4$ alcohol (ethanol)/silicone oil (DC 345). Incorporation of small amounts of a pharmacologically or cosmetically active agent of the invention or of a protective agent of the invention will only insignificantly affect the area of stability. Carrier composition CC consisting of 40% by weight of polar lipid Lipoid S75, 30% by weight of ethanol and 30% by weight of silicone oil DC 345 is an example of a stable carrier composition.

EXAMPLE 10

Phospholipid Based Carrier Compositions

Phospholipid was dissolved in mixtures of DC 345 volatile silicone oil and alcohol. The lipid was accurately weighed and mixed with silicone oil and alcohol. The mixture was gently agitated at 40° C. until a homogenous, clear and colourless or slightly yellow liquid was obtained. Table 4a shows examples of compositions based on phosphatidyl cholines and Table 4b compositions based on phosphatidyl ethanolamines.

TABLE 4a

Carrier compositions based on phosphatidyl cholines

| Composition | Lipid | % w/w | DC 345, % w/w | EtOH, % w/w |
|---|---|---|---|---|
| PC-1 | DMPC | 3.8 | 91.4 | 4.8 |
| PC-2 | DMPC | 7.9 | 82.9 | 9.2 |
| PC-3 | DMPC | 16.5 | 62.6 | 20.9 |
| PC-4 | DMPC | 33.3 | 33.4 | 33.4 |
| PC-5 | DOPC | 23.0 | 57.8 | 19.3 |
| PC-6 | DOPC | 22.4 | 38.8 | 38.8 |
| PC-7 | DPPC | 16.5 | 41.7 | 41.7 |

TABLE 4b

Carrier compositions based on phosphatidyl ethanolamines

| Composition | Lipid | % w/w | DC 345, % w/w | EtOH, % w/w | IPA, % w/w |
|---|---|---|---|---|---|
| PE-1 | DOPE | 4.5 | 90.7 | | 4.8 |
| PE-2 | DOPE | 4.6 | 90.6 | 4.9 | |
| PE-3 | DOPE | 7.0 | 83.7 | 9.3 | |
| PE-4 | DOPE | 10.3 | 80.8 | 9.0 | |
| PE-5 | DOPE | 14.9 | 63.8 | 21.3 | |

EXAMPLE 11

Acylglycerol Based Carrier Compositions

Commercially available monoglyceride products are mixtures of monoacyl-, diacyl- and small amounts of triacylglycerols. The acylglycerol products were dissolved in mixtures of DC 345 volatile silicone oil and alcohol. The lipid was accurately weighed and mixed with silicone oil and alcohol. The mixture was gently agitated at 40° C. until a homogenous, clear and colourless liquid was obtained. Table 5 shows examples of compositions based on acylglycerols.

TABLE 5

Carrier compositions based on acylglycerols

| Composition | Lipid | % w/w | DC 345, % w/w | EtOH, % w/w | IPA, % w/w |
|---|---|---|---|---|---|
| MG-1 | MCM | 13.6 | 86.4 | | |
| MG-2 | MCM | 9.8 | 87.5 | | 2.7 |
| MG-3 | MCM | 21.6 | 74.5 | 3.9 | |
| MG-4 | MCM | 41.2 | 44.1 | 14.7 | |
| MG-5 | MOG | 4.7 | 92.9 | | 2.5 |
| MG-6 | MOG | 4.6 | 91.7 | 3.7 | |
| MG-7 | MOG | 3.6 | 91.6 | 4.8 | |
| MG-8 | MOG | 9.6 | 81.3 | 9.0 | |
| MG-9 | MOG | 19.0 | 60.7 | 20.2 | |
| MG-10 | MOG | 38.3 | 30.8 | 30.8 | |

EXAMPLE 12

Carrier Compositions Based on Cholesterol

Compositions comprising cholesterol were prepared by mixing with DC 345 volatile silicone oil and alcohol. The lipid was accurately weighed and mixed with silicone oil and alcohol. The mixture was gently agitated at 40° C. until a homogenous, clear and colourless liquid was obtained. Table 6 shows examples of compositions based on cholesterol.

TABLE 6

Carrier compositions based on cholesterol

| Composition | Cholesterol, % w/w | DC 345, % w/w | EtOH, % w/w |
|---|---|---|---|
| Chol-1 | 1.4 | 88.8 | 9.9 |
| Chol-2 | 2.1 | 73.4 | 24.5 |
| Chol-3 | 3.0 | 48.5 | 48.5 |

EXAMPLE 13

Carrier Compositions Based on Galactolipid Rich Materials

Two examples of galactolipid rich materials were used to prepare mixtures with DC 345 volatile silicone oil and alcohols. The lipid was accurately weighed and mixed with silicone oil and alcohols. The mixture was gently agitated at 40° C. until a homogenous, clear and slightly yellow to brownish yellow liquid was obtained. Table 7 shows examples of compositions based on galactolipid rich lipids.

TABLE 7

Carrier compositions based on galactolipid rich materials

| Composition | Lipid | % w/w | DC 345, % w/w | EtOH, % w/w | IPA, % w/w |
|---|---|---|---|---|---|
| GL-1 | CPL-GL | 4.9 | 71.3 | 23.8 | |
| GL-2 | CPL-GL | 36.0 | 32.0 | 32.0 | |
| GL-3 | O65 | 3.3 | 73.4 | 4.7 | 18.7 |

EXAMPLE 14

Carrier Compositions Based on Lipid Combinations

The ability to combine lipids with different properties in volatile silicon oil/alcohol mixtures was tested. The lipid materials were accurately weighed and mixed with silicone oil and alcohol. The mixture was gently agitated at 40° C. until a homogenous, clear and colourless or slightly yellow liquid was obtained. Table 8 shows examples of compositions based on various combinations of lipids.

TABLE 8

Carrier compositions based on lipid combinations

| Composition | Lipid 1 | % w/w | Lipid 2 | % w/w | DC 345, % w/w | EtOH, % w/w | IPA, % w/w |
|---|---|---|---|---|---|---|---|
| Comb-1 | IPM | 8.9 | DOPC | 8.3 | 78.7 | 4.1 | |
| Comb-2 | IPM | 9.0 | DOPE | 5.2 | 81.5 | 4.3 | |
| Comb-3 | MCM | 6.9 | DOPC | 5.8 | 82.9 | 4.4 | |
| Comb-4 | MOG | 10.3 | DOPC | 0.9 | 85.1 | | 3.7 |
| Comb-5 | MCM | 8.9 | Chol | 1.0 | 79.8 | 10.3 | |

EXAMPLE 15

Carrier Compositions Based on Commercially Available Lecithin

TABLE 9

Carrier compositions based on lecithin

| Composition | Lecithin | % w/w | DC 345, % w/w | EtOH, % w/w | IPA, % w/w |
|---|---|---|---|---|---|
| Lec-1 | S45 | 5.6 | 89.7 | 4.7 | |
| Lec-2 | S45 | 9.9 | 81.1 | 9.0 | |
| Lec-3 | S45 | 30.3 | 52.3 | 17.4 | |
| Lec-4 | S45 | 35.8 | 32.1 | 32.1 | |
| Lec-5 | S75 | 14.8 | 76.5 | 4.0 | 4.7 |
| Lec-6 | S75 | 25.4 | 63.4 | 7.0 | 4.2 |
| Lec-7 | S75 | 16.3 | 75.3 | 8.4 | |
| Lec-8 | S75 | 43.4 | 42.5 | 14.2 | |
| Lec-9 | S75 | 39.3 | 30.4 | 30.4 | |
| Lec-10 | S100 | 13.1 | 65.2 | 21.7 | |
| Lec-11 | S100 | 27.3 | 36.3 | 36.3 | |

Commercially available lecithin products are in mixtures of polar lipids (mainly phospholipids) and non-polar lipids (mainly triglycerides). The materials used in the following examples are all obtained from soy beans and contain phosphatidyl choline as the main polar lipid. The lipid was accurately weighed and mixed with silicone oil and alcohol. The mixture was gently agitated at 40° C. until a homogenous, clear and yellow or brownish yellow liquid was obtained. Table 9 shows examples of compositions based on lecithins.

EXAMPLE 16

Carrier Compositions with Different Silicone Oils

The possibility to use different volatile silicone oils was tested by replacing DC 345 by two other silicone oils, DC 245 and DC 246. The lipid was weighed and mixed with silicone oil and alcohol. The mixture was gently agitated at 40° C. until a homogenous, clear and colourless liquid was obtained. Table 10 shows examples of compositions comprising DC 245 and DC 246.

TABLE 10

Carrier compositions with volatile silicone oils DC 245 and DC 246

| Composition | Silicone oil | % w/w | Lipid | % w/w | EtOH, % w/w | IPA, % w/w |
|---|---|---|---|---|---|---|
| Sil-1 | DC 245 | 81.8 | DOPE | 9.1 | 9.1 | |
| Sil-2 | DC 245 | 88.0 | MCM | 5.1 | | 6.9 |
| Sil-3 | DC 245 | 94.0 | MCM | 2.2 | | 3.8 |
| Sil-4 | DC 246 | 83.3 | DOPE | 7.4 | 9.3 | |

EXAMPLE 17

Carrier Compositions Based on Lipids and Small Amounts of Water

TABLE 11

Carrier compositions with small amounts of water

| Composition | Lipid | % w/w | Water, % w/w | DC345, % w/w | EtOH, % w/w | IPA, % w/w |
|---|---|---|---|---|---|---|
| Wat-1 | DMPC | 7.0 | 4.7 | 79.5 | 8.8 | |
| Wat-2 | DMPG | 2.3 | 5.3 | 69.4 | 23.1 | |

The possibility to add small amounts of water to the vehicles of the invention was tested. The lipid was accurately weighed and mixed with silicone oil and alcohol. A small amount of water and optionally isopropanol was added. The mixture was gently agitated at 40° C. until a homogenous, clear and colourless or brownish yellow liquid was obtained. Table 11 shows examples of compositions with small amounts of water.

EXAMPLE 18

DPK-060 Peptide Compositions in Silicone Oil/Lipid Vehicles

Accurately weighed amounts of the peptide DPK-060 were dissolved in mixtures of lipid, glycerol, 1,2-propanediol and ethanol at 40° C. under agitation. Silicone oil (DC 345) and isopropanol was added and the mixture was gently agitated at 40° C. until a homogenous, clear and colourless to brownish yellow liquid was obtained. Table 12 presents representative examples of DPK-060 compositions.

TABLE 12

DPK-060 peptide compositions in silicone oil/lipid vehicles

| Composition | DPK-060 % w/w | Lipid | % w/w | Gro % w/w | PD % w/w | DC 345 % w/w | EtOH % w/w | IPA % w/w | % active/nonvol.* |
|---|---|---|---|---|---|---|---|---|---|
| KL-DPK-21 | 0.033 | S75 | 3.9 | 6.4 | | 58.2 | 13.0 | 18.5 | 0.32 |
| KL-DPK-22 | 0.199 | S75 | 5.7 | 10.1 | 2.8 | 39.3 | 12.5 | 29.3 | 1.06 |
| KL-DPK-23 | 0.056 | S45 | 3.9 | 6.6 | | 56.8 | 12.5 | 20.1 | 0.53 |
| KL-DPK-24 | 0.129 | S45 | 5.8 | 9.8 | 2.9 | 39.5 | 12.6 | 29.3 | 0.69 |
| KL-DPK-25 | 0.095 | DOPC | 3.8 | 6.6 | | 56.2 | 13.0 | 20.3 | 0.90 |
| KL-DPK-26 | 0.272 | DOPC | 6.8 | 10.3 | 2.8 | 40.8 | 13.1 | 26.0 | 1.34 |
| KL-DPK-27 | 0.036 | 065 | 4.0 | 6.3 | | 54.3 | 11.6 | 23.7 | 0.35 |
| KL-DPK-28 | 0.058 | 065 | 5.6 | 9.6 | 2.8 | 38.9 | 11.4 | 31.5 | 0.32 |
| KL-DPK-29 | 0.096 | DOPE | 4.4 | 6.9 | | 57.8 | 12.9 | 17.9 | 0.84 |
| KL-DPK-31 | 0.125 | DMPC | 4.3 | 6.4 | | 57.1 | 12.7 | 19.3 | 1.15 |
| KL-DPK-40 | 0.167 | S75 | 4.6 | 6.3 | 6.1 | 42.6 | 13.9 | 26.3 | 0.98 |
| KL-DPK-42 | 0.184 | S45 | 5.7 | 10.1 | 2.9 | 40.0 | 11.5 | 29.5 | 0.97 |
| KL-DPK-43 | 0.188 | DOPC | 5.7 | 9.5 | 3.7 | 40.9 | 11.9 | 28.0 | 0.98 |
| KL-DPK-45 | 0.192 | DOPE | 5.9 | 10.3 | 3.1 | 41.7 | 11.8 | 27.1 | 0.99 |
| KL-DPK-47 | 0.189 | DMPC | 5.9 | 10.2 | 3.1 | 40.9 | 11.5 | 28.2 | 0.97 |
| KL-DPK-49 | 0.168 | SM | 4.1 | 6.5 | | 56.0 | 12.7 | 20.6 | 1.57 |
| KL-DPK-50 (placebo) | — | S75 | 4.7 | 6.2 | 6.1 | 42.8 | 13.7 | 26.4 | — |
| KL-DPK-51 (placebo) | — | DOPE | 4.2 | 6.6 | | 58.9 | 13.2 | 17.1 | — |
| KL-DPK-52 | 0.105 | DOPE | 4.0 | 6.6 | | 57.6 | 13.0 | 18.7 | 0.98 |
| KL-DPK-53 | 0.107 | DMPC | 4.2 | 6.6 | | 58.3 | 13.0 | 17.7 | 0.97 |

*Concentration of DPK-060 in % w/w of the non-volatile part of the composition

TABLE 11-continued

Carrier compositions with small amounts of water

| Composition | Lipid | % w/w | Water, % w/w | DC345, % w/w | EtOH, % w/w | IPA, % w/w |
|---|---|---|---|---|---|---|
| Wat-3 | DOPE | 6.8 | 2.5 | 58.1 | 14.9 | 17.7 |
| Wat-4 | S75 | 9.7 | 4.4 | 53.7 | 10.8 | 21.5 |
| Wat-5 | S75 | 5.5 | 2.0 | 72.9 | 8.1 | 11.4 |

EXAMPLE 19

LL-37 Peptide Compositions in Silicone Oil/Lipid Vehicles

Accurately weighed amounts of the peptide LL-37 were dissolved in mixtures of lipid, glycerol and ethanol at 40° C. under agitation. Silicone oil (DC 345) and isopropanol was added and the mixture was gently agitated at 40° C. until a homogenous, clear and slightly yellow to brownish yellow liquid was obtained. Table 13 presents representative examples of LL-37 compositions.

TABLE 13

LL-37 peptide compositions in silicone oil/lipid vehicles

| Composition | LL-37 % w/w | Lipid | % w/w | Gro % w/w | DC 345 % w/w | EtOH % w/w | IPA % w/w | % active/ nonvol* |
|---|---|---|---|---|---|---|---|---|
| KL-LL37-1 | 0.202 | S75 | 6.9 | 7.1 | 48.5 | 23.3 | 14.0 | 1.42 |
| KL-LL37-2 | 0.184 | DOPE | 5.3 | 8.0 | 49.3 | 26.2 | 11.1 | 1.37 |

*Concentration of LL-37 in % w/w of the non-volatile part of the composition

EXAMPLE 20

Oxytocin Compositions in Silicone Oil/Lipid Vehicles

Accurately weighed amounts of oxytocin were dissolved in mixtures of lipid, glycerol and ethanol at 40° C. under agitation. Silicone oil (DC 345) and optionally isopropanol was added and the mixture was gently agitated at 40° C. until a homogenous, clear and colourless to brownish yellow liquid was obtained. Table 14 presents representative examples of oxytocin compositions.

TABLE 14

Oxytocin compositions in silicone oil/lipid vehicles

| Composition | Oxytocin % w/w | Lipid 1 | % w/w | Lipid 2 | % w/w | Gro % w/w | DC 345 % w/w | EtOH % w/w | IPA % w/w | % active/ nonvol* |
|---|---|---|---|---|---|---|---|---|---|---|
| Ox-1 | 0.139 | DOPE | 5.9 | MCM | 10.8 | | 70.6 | 12.6 | | 0.83 |
| Ox-2 | 0.090 | DOPE | 4.4 | MCM | 10.0 | 8.1 | 46.4 | 8.3 | 22.8 | 0.40 |
| Ox-3 | 0.126 | MCM | 22.1 | | | | 66.3 | 11.5 | | 0.56 |
| Ox-4 | 0.094 | MCM | 3.9 | | | 8.6 | 48.8 | 7.1 | 31.5 | 0.74 |
| Ox-5 | 0.078 | MCM | 5.1 | | | | 58.2 | 23.4 | 13.2 | 1.51 |
| Ox-6 | 0.100 | MOG | 25.6 | | | | 64.0 | 10.3 | | 0.39 |
| Ox-7 | 0.161 | S75 | 6.6 | | | | 80.0 | 13.3 | | 2.40 |
| Ox-8 | 0.088 | S75 | 5.0 | | | 8.5 | 51.7 | 8.6 | 26.1 | 0.65 |
| Ox-9 | 0.129 | | | | | 8.6 | 51.0 | 8.9 | 31.4 | 1.47 |
| Ox-10 | 0.178 | | | | | | 85.8 | 14.0 | | 100 |

*Concentration of oxytocin in % w/w of the non-volatile part of the composition

EXAMPLE 21

Hydrocortisone Compositions in Silicone Oil/Lipid Vehicles

An accurately weighed amount of hydrocortisone was dissolved in a mixture of lipid and ethanol at 40° C. under agitation. Silicone oil (DC 345) and isopropanol was added and the mixture was gently agitated at 40° C. until a homogenous, clear and yellow liquid was obtained. Table 15 presents a representative example of hydrocortisone compositions.

TABLE 15

Hydrocortisone composition in silicone oil/lipid vehicles

| Composition | Hydrocortisone % w/w | Lipid | % w/w | DC 345 % w/w | EtOH % w/w | IPA % w/w | % active/ nonvol* |
|---|---|---|---|---|---|---|---|
| HC-1 | 0.093 | S75 | 4.8 | 65.2 | 14.8 | 15.1 | 1.93 |

*Concentration of hydrocortisone in % w/w of the non-volatile part of the composition

EXAMPLE 22

Dihydroxyacetone Compositions in Silicone Oil/Lipid Vehicles

An accurately weighed amount of dihydroxyacetone was dissolved in a mixture of lipid and ethanol at 40° C. under agitation. Silicone oil (DC 345) and isopropanol was added and the mixture was gently agitated at 40° C. until a homogenous, clear and yellow liquid was obtained. Table 16 presents a representative example of dihydroxyacetone compositions.

TABLE 16

Dihydroxyacetone composition in silicone oil/lipid vehicles

| Composition | Dihydroxyacetone % w/w | Lipid | % w/w | DC 345 % w/w | EtOH % w/w | IPA % w/w | % active/ nonvol* |
|---|---|---|---|---|---|---|---|
| DA-1 | 1.03 | MCM | 4.4 | 76.8 | 8.9 | 8.8 | 19.0 |

*Concentration of dihydroxyacetone in % w/w of the non-volatile part of the composition

EXAMPLE 23

Lidocaine Compositions in Silicone Oil/Lipid Vehicles

An accurately weighed amount of lidocaine was dissolved in a mixture of lipid and ethanol at 40° C. under agitation. Silicone oil (DC 345) and optionally isopropanol was added and the mixture was gently agitated at 40° C. until a homogenous, clear and colourless to yellow liquid was obtained. Table 17 presents representative examples of lidocaine compositions.

TABLE 17

Lidocaine compositions in silicone oil/lipid vehicles

| Composition | Lidocaine %/w/w | Lipid 1 | % w/w | Lipid 2 | % w/w | DC 345 % w/w | EtOH % w/w | IPA % w/w | % active/nonvol* |
|---|---|---|---|---|---|---|---|---|---|
| KL-LK-1 | 0.7 | S75 | 7.6 | | | 65.4 | 7.5 | 18.8 | 8.8 |
| KL-LK-2 | 0.8 | S75 | 2.8 | | | 59.8 | 11.4 | 25.3 | 22.2 |
| KL-LK-6 | 11.5 | S75 | 13.7 | | | 65.3 | 9.5 | | 45.8 |
| KL-LK-7 | 5.1 | DOPE | 1.3 | | | 88.7 | 5.0 | | 79.9 |
| KL-LK-8 | 5.1 | DOPE | 10.2 | | | 74.9 | 9.8 | | 33.0 |
| KL-LK-9 | 4.7 | MCM | 1.1 | Chol | 0.5 | 87.8 | 5.9 | | 74.4 |
| KL-LK-10 | 4.8 | | | | | 90.3 | 4.9 | | 100 |
| KL-LK-11 | 5.0 | MCM | 8.9 | Chol | 1.0 | 75.2 | 10.0 | | 33.5 |
| KL-LK-12 | 5.0 | S75 | 15.0 | | | 70.1 | 9.9 | | 25.0 |
| KL-LK-13 | 5.0 | DOPE | 5.2 | | | 79.6 | 10.2 | | 48.7 |
| KL-LK-14 | 5.0 | | | | | 85.0 | 10.0 | | 100 |
| KL-LK-16 | 20.2 | MCM | 20.8 | | | 50.4 | 8.6 | | 49.4 |

*Concentration of lidocaine in % w/w of the non-volatile part of the composition

EXAMPLE 24

Control of Transepidermal Water Loss

Three lipid layer forming compositions of the invention termed A, B, C (Table 18) were tested for their effect on transepidermal water loss (TEWL) from a skin surface. Their effect was compared with that of white vaseline (ACO hud, Sweden), a conventional agent for TEWL. The compositions were applied to the skin of ten healthy individuals, 5 women and 5 men; mean age 34 years, SD 18 years, who showed no evidence of skin disease. Prior to application, the volar aspects of their forearms were rapidly cleansed with paper tissue soaked in pure alcohol. Five rectangular areas of 2×2 cm were marked on the volar forearm with a pencil and measured for basal TEWL. The compositions and vaseline were applied to the areas in a randomized manner; one of the areas was left as an untreated control. Two dosages were studied, 3 µl/cm² and 6 µl/cm². Vaseline was used in half of the amount, i.e. 1.5 µl/cm² and 3 µl/cm². The high dose was applied on the right forearm, and the low dose on the left forearm. The products were dispensed onto the surface by means of a displacement micro-pipette (Gilson). The compositions were applied in small droplets onto the area; evaporation was facilitated by slightly blowing at the surface. Vaseline was spread by fingertip.

TABLE 18

Compositions tested for control of transepidermal water loss (% by weight)

| Composition # | MCM | Polar lipid | EtOH | DC345 |
|---|---|---|---|---|
| 1 | | 15 (S75) | 10 | 75 |
| 2 | 9 | 1 (Chol) | 10 | 80 |
| 3 | | 5 (DOPE) | 10 | 85 |

Figure 2:
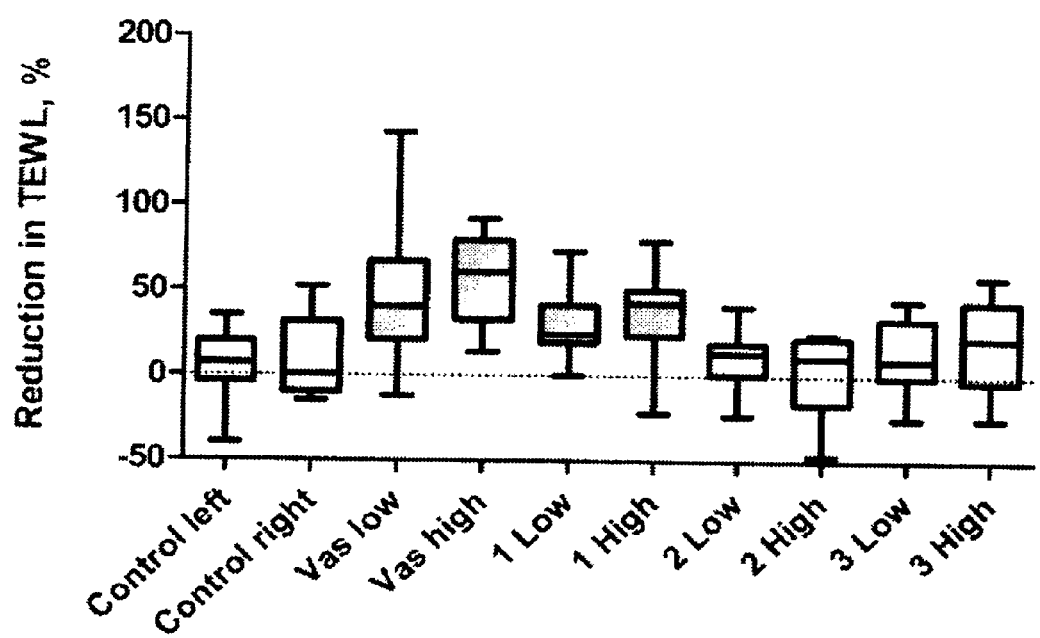
FIG. 2 is a diagram showing change in transepidermal water loss (TEWL) for three compositions of the invention and vaseline as reference.
Figure 3:
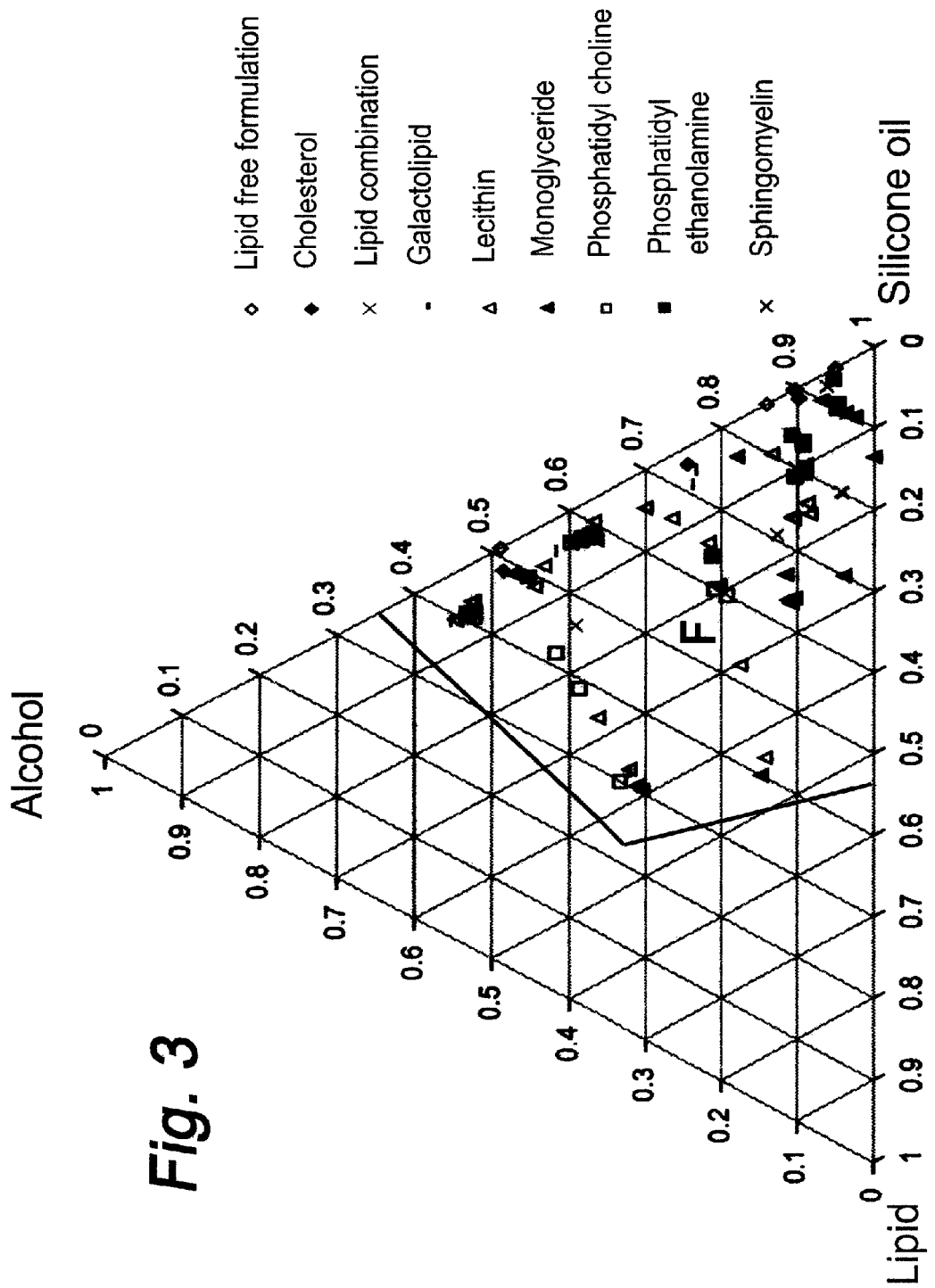
FIG. 3 is another ternary phase diagram of lipid layer forming compositions of the invention including carrier compositions and compositions comprising active agent.

TEWL was measured before application and 30 min after application by use of DermaLab equipment (open chamber; Cortex Technology, Hadsund, Denmark). The recorded reduction of transepidermal water loss is shown in FIG. 2. The composition 1 of the invention was comparable in effect to Vaseline while compositions 2 and 3 of the invention exerted no significant effect on TEWL.

The invention claimed is:

1. A homogeneous topical composition which forms a lipid layer when applied to skin or mucous membrane, the composition comprising
volatile silicone oil,
from 10% by weight to 30% by weight of phospholipid, and
16% by weight to 45% by weight of ethanol,
wherein the silicone oil has a boiling point above 180° C. and wherein the content of volatile silicone oil is 40% by weight to 72.9% by weight of the composition, and wherein the composition comprises less than 1% by weight of water.

2. The composition of claim 1, wherein the silicone oil has a heat of vaporization (kJ/kg) at 25° C. of from 100 kJ/kg to 300 kJ/kg.

3. The composition of claim 1, wherein the silicone oil has a boiling point above 200° C.

4. The composition of claim 1, wherein the volatile silicone oil comprises one of decamethylcyclopentasiloxane and dodecamethylcyclohexasiloxane.

5. The composition of claim 1, said composition comprising water in an amount of 0.5% by weight or less.

6. The composition of claim 5, comprising less than 0.2% by weight of water.

7. The composition of claim 1, said composition further comprising a cosmetically active agent.

8. The composition of claim 1, said composition further comprising a protective agent.

9. The composition of claim 1, comprising from 10% by weight to 30% by weight of phospholipid, from 16% by weight to 45% by weight of ethanol, and the remainder being silicone oil, wherein the composition is a carrier composition not comprising a pharmacologically or cosmetically active agent or a protective agent.

10. The composition of claim 1, further comprising a pharmacologically active agent selected from the group consisting of: an antimicrobial agent, an antibiotic; an antimycotic agent; an antibacterial agent; an antifungal agent; an antiviral agent; an antiseptic; an anti-phlogistic; an antipruritic agent; an antipsoriatic agent; an antitussive agent; an anti-alopecia agent; an anti-acne agent; an anti-inflammatory agent; an anti-ulcer agent; and a local anaesthetic.

11. The composition of claim 7, wherein the agent is a cosmetically active agent selected from the group consisting of: antiperspirant; antisudoral agent; antidandruff agent; glidant; moisturizing agent.

12. The composition of claim 8, wherein the agent is a protective agent selected from the group consisting of: UV-absorbing agent, insect repellent, antibacterial agent, antifungal agent; antiviral agent, anti-nematode agent.

13. A topical composition which forms a lipid layer when applied to skin or mucous membrane, the composition comprising
  volatile silicone oil,
  from 10% by weight to 30% by weight of phospholipid, and
  16% by weight to 45% by weight of ethanol,
wherein the silicone oil has a boiling point above 180° C. and wherein the content of volatile silicone oil is 40% by weight to 72.9% by weight of the composition, wherein the composition comprises no added water.

14. The composition of claim 1, wherein the composition is clear.

15. The composition of claim 13, wherein the composition is clear.

* * * * *